(12) United States Patent
Park et al.

(10) Patent No.: US 10,988,847 B2
(45) Date of Patent: Apr. 27, 2021

(54) APPARATUS AND METHOD OF PREPARING CARBONATE AND/OR FORMATE FROM CARBON DIOXIDE

(71) Applicant: Korea Institute of Energy Research, Daejeon (KR)

(72) Inventors: Ki Tae Park, Daejeon (KR); Soon Kwan Jeong, Daejeon (KR); Seong Pil Kang, Daejeon (KR); Hak Joo Kim, Daejeon (KR); Min Hye Youn, Sejong-si (KR)

(73) Assignee: KOREA INSTITUTE OF ENERGY RESEARCH, Daejeon (KR)

( * ) Notice: Subject to any disclaimer, the term of this patent is extended or adjusted under 35 U.S.C. 154(b) by 241 days.

(21) Appl. No.: 15/804,569

(22) Filed: Nov. 6, 2017

(65) Prior Publication Data
US 2018/0127886 A1 May 10, 2018

(30) Foreign Application Priority Data
Nov. 4, 2016 (KR) .................. 10-2016-0146966

(51) Int. Cl.
 *C25B 3/25* (2021.01)
 *C25B 15/02* (2021.01)
 (Continued)

(52) U.S. Cl.
 CPC ............ *C25B 3/25* (2021.01); *B01D 19/0036* (2013.01); *B01D 19/0068* (2013.01);
 (Continued)

(58) Field of Classification Search
 CPC .... C25B 3/04; C25B 3/00; C25B 3/25; C25B 3/26
 See application file for complete search history.

(56) References Cited

U.S. PATENT DOCUMENTS

| 4,496,443 A * | 1/1985 | Mack ................ C05D 5/00 119/51.5 |
| 2008/0223727 A1* | 9/2008 | Oloman ............ B01D 53/326 205/413 |

(Continued)

FOREIGN PATENT DOCUMENTS

| JP | 2003-306788 A | 10/2003 |
| KR | 10-2013-0112037 A | 10/2013 |
| KR | 10-2015-0055033 A | 5/2015 |

OTHER PUBLICATIONS

Kim et al., "Analysis on the effect of operating conditions on electrochemical conversion of carbon dioxide to formic acid", International Journal of Hydrogen Energy, 2014, 7 pages. (http://dx.doi.org/10.1016/j.ijhydene.2014.03.145).

(Continued)

*Primary Examiner* — Nicholas A Smith
(74) *Attorney, Agent, or Firm* — Birch, Stewart, Kolasch & Birch, LLP

(57) ABSTRACT

The present invention relates to an apparatus and method of preparing carbonate and/or formate from carbon dioxide. The apparatus of preparing carbonate and/or formate from carbon dioxide ($CO_2$), comprising: an electrolysis reactor comprising (i) an anode which contains an aqueous solution of a Group I metal salt as an electrolytic solution, (ii) an ion-exchange membrane through which metal cations derived from the Group I metal salt and water flow from an anode to a cathode, (iii) a cathode, and (iv) a gas diffusion layer which supplies a carbon dioxide-containing gas to the cathode; a power supply unit of applying a voltage between the anode and the cathode; a first gas-liquid separator of recovering the electrolytic solution from the products formed in the anode; a second gas-liquid separator of recovering carbonate and/or formate from the products formed in the cathode; a pH meter of measuring the pH of (Continued)

the electrolytic solution recovered from the first gas-liquid separator; a first reactant supply unit of supplying (a) the electrolytic solution recovered from the first gas-liquid separator and (b) the aqueous solution of the Group I metal salt with which the recovered electrolytic solution is replenished according to the pH of the electrolytic solution, to the anode; and a second reactant supply unit of supplying carbon dioxide or a mixer comprising carbon dioxide and water vapor to the cathode; wherein, when a voltage is applied between the anode and the cathode, in the anode, water undergoes electrolysis to generate hydrogen ions, oxygen, and electrons, and metal cations in the Group I metal salt are substituted with the hydrogen ions, while the generated metal cations move to the cathode through the ion-exchange membrane and the electrons move to the cathode through an external electric line; and in the cathode, carbon dioxide, water, metal cations, and electrons are reacted and produce carbonate and/or formate.

15 Claims, 4 Drawing Sheets

(51) Int. Cl.
*B01D 19/00* (2006.01)
*C25B 9/23* (2021.01)
*C25B 3/26* (2021.01)
*C01B 32/60* (2017.01)
*C25B 1/04* (2021.01)
*C01B 32/50* (2017.01)
*C07C 45/41* (2006.01)
*C07C 53/02* (2006.01)

(52) U.S. Cl.
CPC .......... *B01D 19/0084* (2013.01); *C01B 32/50* (2017.08); *C01B 32/60* (2017.08); *C07C 45/41* (2013.01); *C07C 53/02* (2013.01); *C25B 1/04* (2013.01); *C25B 3/26* (2021.01); *C25B 9/23* (2021.01); *C25B 15/02* (2013.01); *Y02E 60/36* (2013.01)

(56) References Cited

U.S. PATENT DOCUMENTS

| | | | | |
|---|---|---|---|---|
| 2011/0114503 | A1* | 5/2011 | Sivasankar | C25B 3/00 205/436 |
| 2014/0251822 | A1* | 9/2014 | Bhavaraju | C25B 3/04 205/441 |
| 2016/0108530 | A1* | 4/2016 | Masel | B01J 41/14 204/265 |
| 2016/0355931 | A1* | 12/2016 | Kaczur | C25B 1/00 |
| 2017/0037522 | A1* | 2/2017 | Kaczur | C25B 1/00 |

OTHER PUBLICATIONS

Lee et al., "Sustainable production of HCOOH via an electrolytic reduction of gas-phase $^{12}CO_2$", Journal of Materials Chemistry A, 2014; DOI: 10.1039/C4TA03893B, 8 pages.

* cited by examiner

[FIG. 1A]
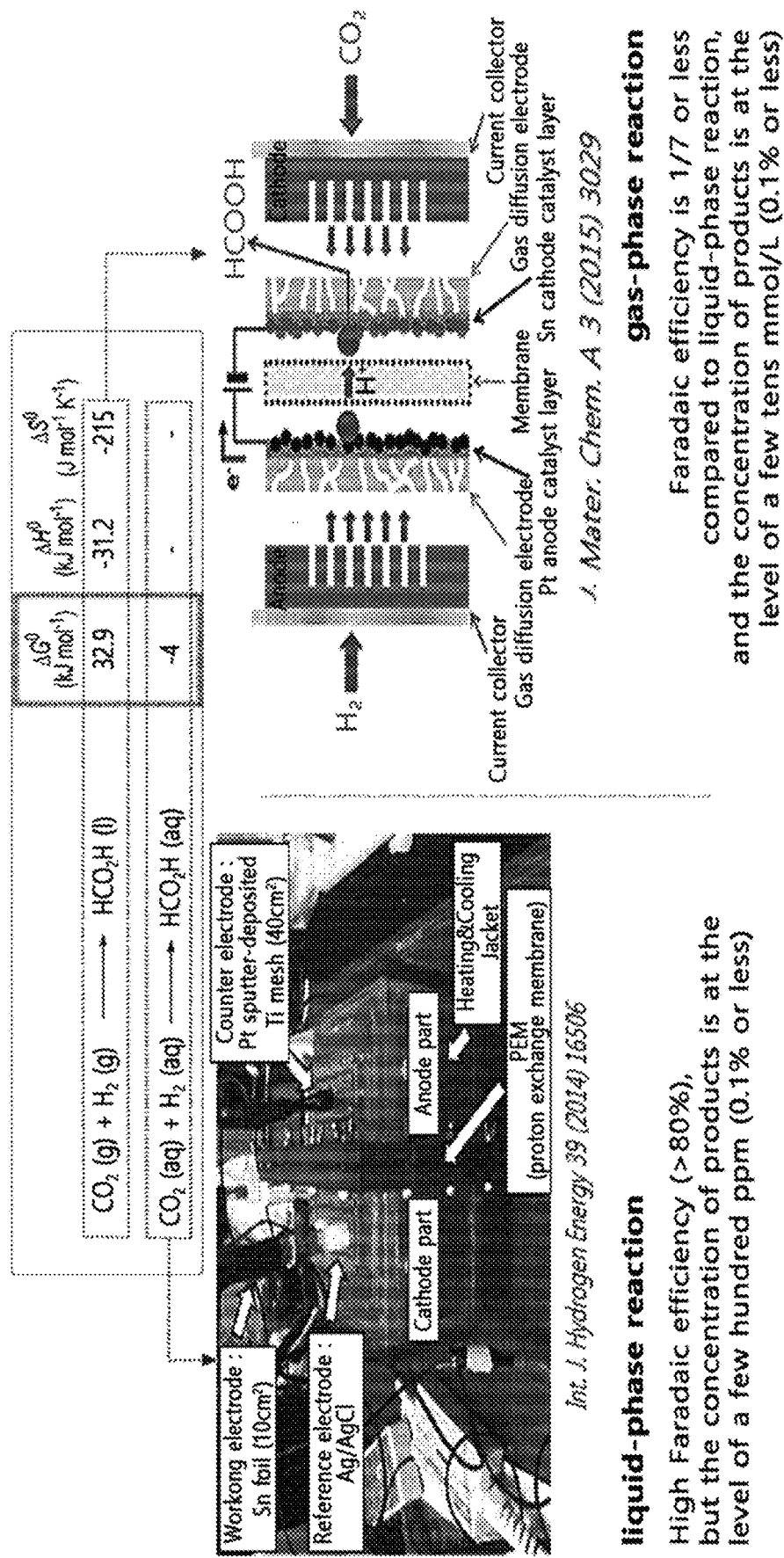

[FIG. 1B]
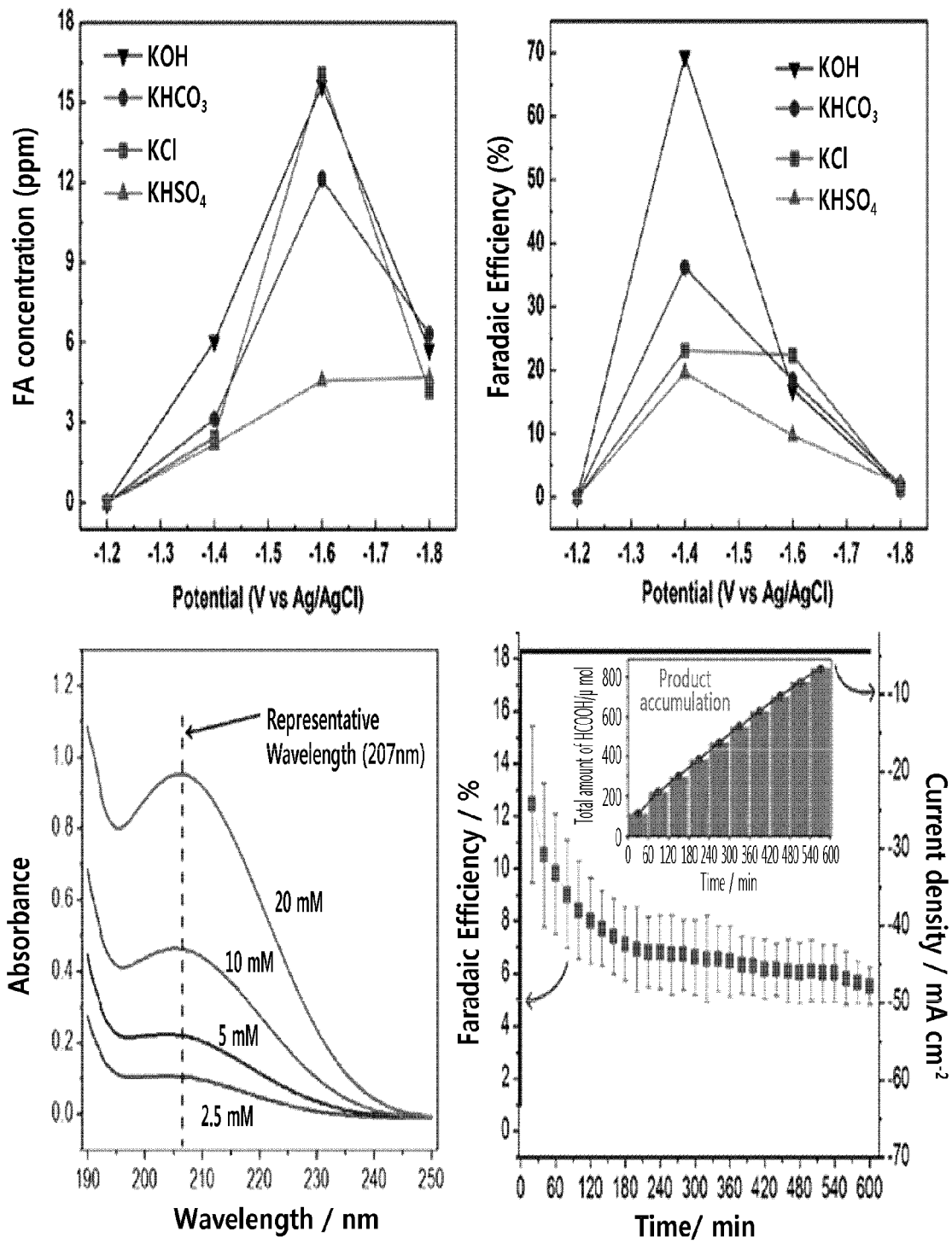

[FIG. 2]
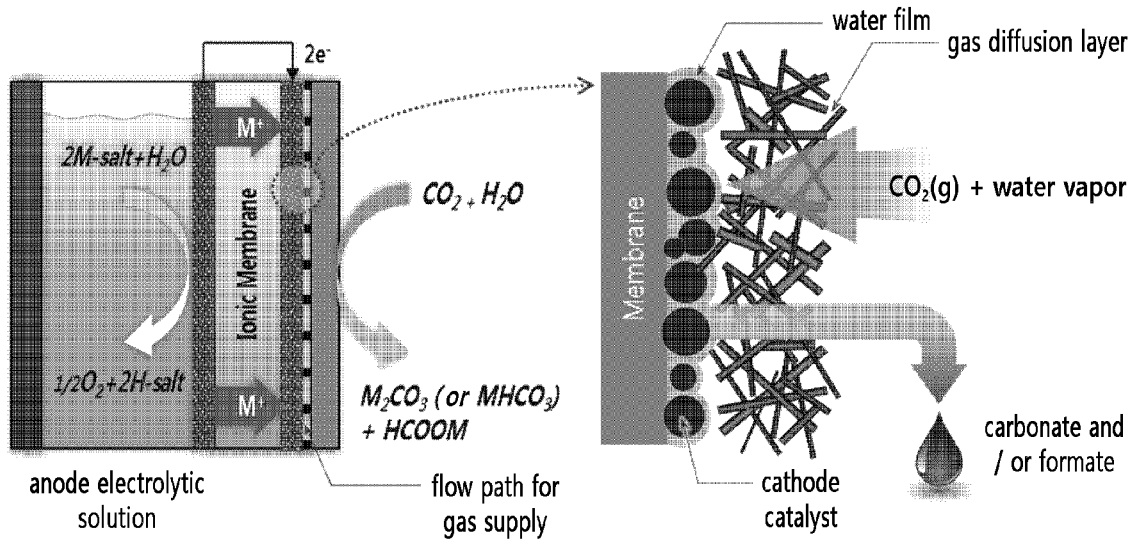
[FIG. 3]
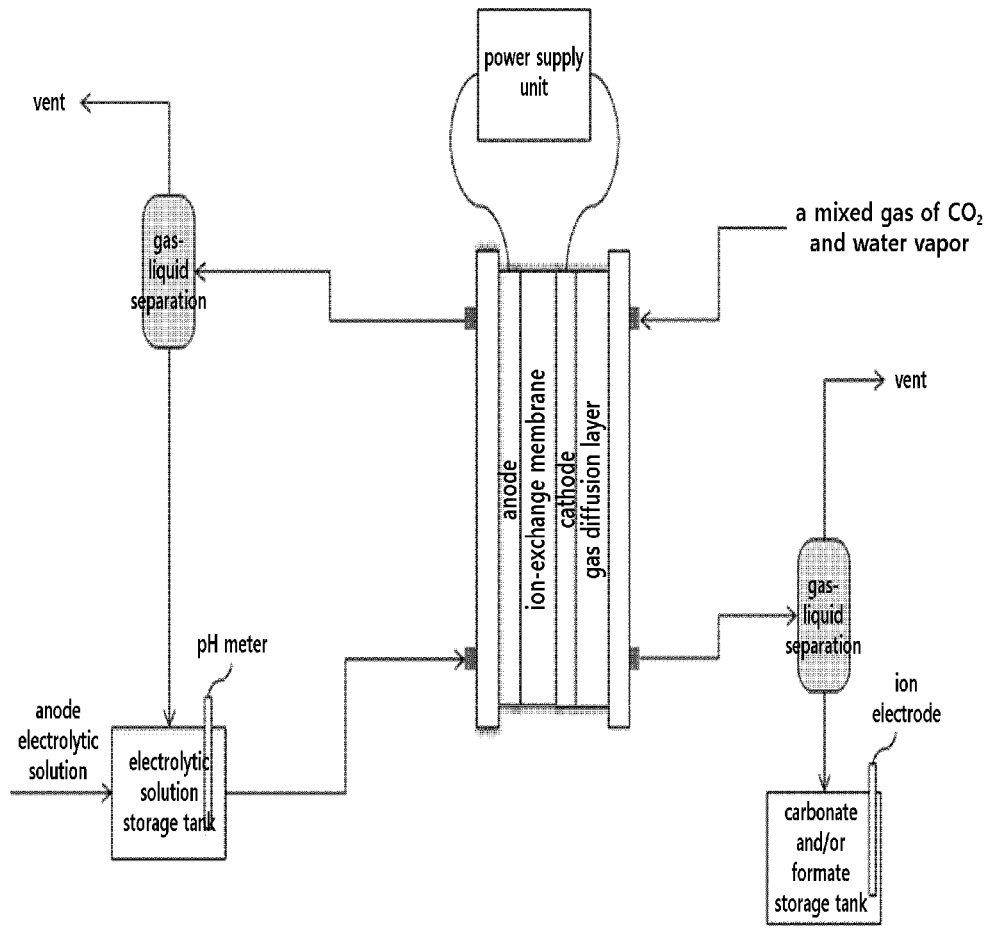

[FIG. 4]
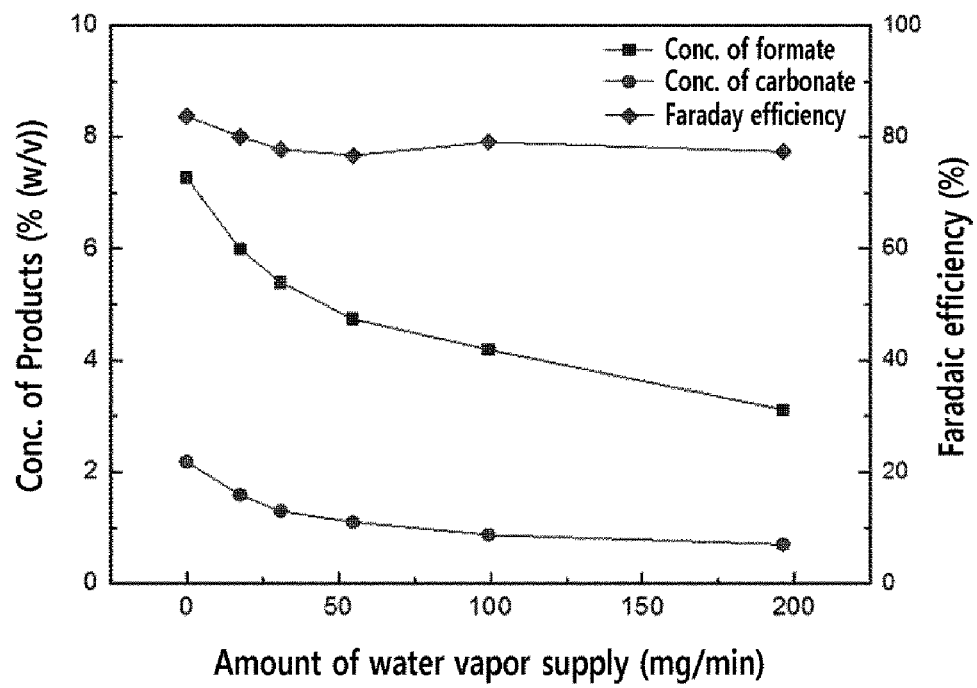

APPARATUS AND METHOD OF PREPARING CARBONATE AND/OR FORMATE FROM CARBON DIOXIDE

CROSS REFERENCE TO RELATED APPLICATION

This non-provisional application claims the benefit under 35 U.S.C. § 119(a) to Patent Application No. 10-2016-0146966, filed in the Republic of Korea on Nov. 4, 2016, all of which is hereby expressly incorporated by reference into the present application.

TECHNICAL FIELD

The present invention relates to an apparatus and method of preparing carbonate and/or formate from carbon dioxide.

BACKGROUND ART

Direct $CO_2$ reduction technologies for storing $CO_2$ emissions from power plants, steel mills, etc. in reservoirs instead of releasing them into the air can be regarded as carbon dioxide capture and storage (CCS), and the treatment of captured $CO_2$ is largely divided into direct storage, utilization or industrial uses, mineral carbonation, etc. Among these, $CO_2$ mineral carbonation technology has the advantage of storing $CO_2$ stably and permanently, but the technology is still regarded as being in the early stages of development, and additionally, it is known to be suitable for the treatment of relatively small- and medium-sized amounts of $CO_2$, and requires a high processing cost.

Meanwhile, the way in which carbon dioxide is reduced electrochemically depends on the methods of ion exchange. Among them, the reduction of electrochemical carbon dioxide using a cation-exchange membrane causes the decomposition of water in the anode to generate oxygen, electrons, and hydrogen cations. At the cathode, carbon dioxide reacts with the electrons and hydrogen cations generated at the anode to cause a reduction reaction and is converted to a different material.

Among the products formed by the reaction of carbon dioxide, the product in liquid form has an advantage in that it has a higher energy density and is easier to handle than the product in gaseous form. In particular, formic acid has the advantage that it can be used in the synthesis of medicines or in the production of paper and pulp as well as having a higher price than other liquid products. Because of this, formic acid has attracted much attention compared to other materials that can be produced by reacting carbon dioxide.

Generally, in the liquid-phase reaction of carbon dioxide, the Faradaic efficiency (or current efficiency) is higher than that of the gas-phase reduction reaction by more than 80%, but the product concentration is as low as several ppm because the product is mixed with a liquid electrolyte (*Int. J. Hydrogen Energy* 39 (2014) 16506). As a result, the product has a very low value and the liquid-phase reaction requires separate separation and concentration processes of the product.

Meanwhile, with regard to the Faradaic efficiency of the gas-phase reaction of carbon dioxide, the highest performance reported so far is 10% (*J. Mater. Chem. A*, 2015, 3, 3029). Additionally, the concentration of the product in the gas-phase reduction of carbon dioxide is also in the range of several mmol/L to several tens of mmol/L (at the level of thousands of ppm) and thus has a very low value as a product. Therefore, the gas-phase reaction requires separate separation and concentration processes.

DISCLOSURE

Technical Problem

An object of the present invention is to provide an apparatus and method of preparing carbonate and formate at a high concentration and/or high Faradaic efficiency through the reduction reaction of carbon dioxide.

Technical Solution

A first aspect of the present invention provides an apparatus of preparing carbonate and/or formate from carbon dioxide ($CO_2$), which includes:

an electrolysis reactor comprising (i) an anode which contains an aqueous solution of a Group I metal salt as an electrolytic solution, (ii) an ion-exchange membrane through which metal cations derived from the Group I metal salt and water flow from an anode to a cathode, (iii) a cathode, and (iv) a gas diffusion layer which supplies a carbon dioxide-containing gas to the cathode;

a power supply unit of applying a voltage between the anode and the cathode;

a first gas-liquid separator of recovering the electrolytic solution from the products formed in the anode;

a second gas-liquid separator of recovering carbonate and/or formate from the products formed in the cathode;

a pH meter of measuring the pH of the electrolytic solution recovered from the first gas-liquid separator;

a first reactant supply unit of supplying (a) the electrolytic solution recovered from the first gas-liquid separator and (b) the aqueous solution of the Group I metal salt with which the recovered electrolytic solution is replenished according to the pH of the electrolytic solution, to the anode; and a second reactant supply unit of supplying carbon dioxide or a mixer comprising carbon dioxide and water vapor to the cathode;

wherein, when a voltage is applied between the anode and the cathode, in the anode, water undergoes electrolysis to generate hydrogen ions, oxygen, and electrons, and metal cations in the Group I metal salt are substituted with the hydrogen ions, while the generated metal cations move to the cathode through the ion-exchange membrane and the electrons move to the cathode through an external electric line; and in the cathode, carbon dioxide, water, metal cations, and electrons are reacted and produce carbonate and/or formate.

A second aspect of the present invention provides a method of preparing carbonate and/or formate from carbon dioxide in an electrolysis reactor, which includes:

(1) supplying an aqueous solution of a Group I metal salt as an electrolytic solution to an anode of the electrolysis reactor;

(2) supplying a carbon dioxide-containing gas to a cathode of the electrolysis reactor;

(3) applying a voltage between the anode and the cathode to generate hydrogen ions, oxygen, and electrons via electrolysis of water in the anode and substituting the metal cations in the Group I metal salt with the hydrogen ions;

(4) transporting the metal cations generated in the anode to the cathode through an ion-exchange membrane and transporting the electrons to the cathode through an external electric line; and (5) reacting carbon dioxide, water, metal cations, and electrons in the cathode to produce carbonate and/or formate; and (6) for the purpose of maintaining the concentration of the Group I metal salt in the electrolytic solution to be supplied to the anode, measuring the pH of the electrolytic solution recovered from the products formed in the anode and replenishing the recovered the electrolytic solution with the aqueous solution of the Group I metal salt according to the pH of the electrolytic solution.

The method of preparing carbonate and/or formate from carbon dioxide ($CO_2$) according to the second aspect of the present invention may be performed in the apparatus of the first aspect of the present invention.

Hereinafter, the present invention will be described in detail.

The electrochemical carbon dioxide conversion is a reaction in which carbon dioxide is reduced to a useful carbon compound through electron transfer by generating a potential difference between the two electrodes by applying electrical energy.

The existing liquid-phase reaction of carbon dioxide has a Faradaic efficiency (or current efficiency) of 80% or higher, which is higher than that of the gas-phase reaction, but the product concentration is as low as several ppm. Meanwhile, since the gas-phase reaction of carbon dioxide is a non-spontaneous reaction, energy efficiency is very low and the Faradaic efficiency is very low to the level of 10%.

The limitations of these gas-phase reactions can be explained thermodynamically as in Reaction Schemes 1 and 2 below.

$$CO_2(g)+H_2(g) \rightarrow HCOOH(l) \Delta G^0 = 32.9 \text{ kJ/mol} \quad \text{[Reaction Scheme 1]}$$

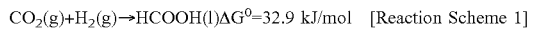

$$CO_2(aq)+H_2(aq) \rightarrow HCOOH(aq) \Delta G^0 = -4 \text{ kJ/mol} \quad \text{[Reaction Scheme 2]}$$

Compared with the reduction reaction of $CO_2$ thermodynamically dissolved in the liquid phase into formic acid, the reduction reaction of $CO_2$ in the gas phase requires higher energy.

For the preparation of carbonate and formate at high concentration and/or high Faradaic efficiency, the apparatus of preparing carbonate and/or formate from carbon dioxide ($CO_2$) according to the present invention includes;

an electrolysis reactor including (i) an anode which contains an aqueous solution of a Group I metal salt as an electrolytic solution, (ii) an ion-exchange membrane through which metal cations derived from the Group I metal salt and water flow from an anode to a cathode, (iii) a cathode, and (iv) a gas diffusion layer which supplies a carbon dioxide-containing gas to the cathode;

a power supply unit of applying a voltage between the anode and the cathode;

a first gas-liquid separator of recovering the electrolytic solution from the products formed in the anode;

a second gas-liquid separator of recovering carbonate and/or formate from the products formed in the cathode;

a pH meter of measuring the pH of the electrolytic solution recovered from the first gas-liquid separator;

a first reactant supply unit of supplying (a) the electrolytic solution recovered from the first gas-liquid separator and (b) the aqueous solution of the Group I metal salt with which the recovered electrolytic solution is replenished according to the pH of the electrolytic solution, to the anode; and a second reactant supply unit of supplying carbon dioxide or a mixer comprising carbon dioxide and water vapor to the cathode.

In the apparatus according to the present invention, when a voltage is applied between the anode and the cathode, in the anode, water undergoes electrolysis to generate hydrogen ions, oxygen, and electrons, and metal cations in the Group I metal salt are substituted with the hydrogen ions, while the generated metal cations move to the cathode through the ion-exchange membrane and the electrons move to the cathode through an external electric line; and in the cathode, carbon dioxide, water, metal cations, and electrons are reacted and produce carbonate and/or formate.

When a voltage is applied between the anode and the cathode, the anode reaction and the cathode reaction may be represented by the following Reaction Schemes 3 and 4.

[Anode Reaction] $2M\text{-salt}+H_2O \rightarrow 2M^+ +2e^- + \frac{1}{2}O_2 + 2H\text{-salt (M: Group I metal)}$ [Reaction Scheme 3]

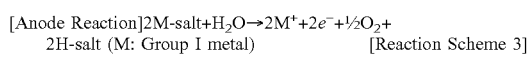

[Cathode Reaction] $2CO_2+H_2O+2M^+ +2e^- \rightarrow M_2CO_3$ (or $MHCO_3$)+HCOOM [Reaction Scheme 4]

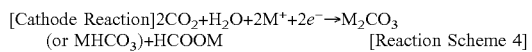

Additionally, for the preparation of carbonate and formate at high concentration and/or high Faradaic efficiency in an electrolysis reactor, the apparatus of preparing carbonate and/or formate from carbon dioxide ($CO_2$) according to the present invention includes;

(1) supplying an aqueous solution of a Group I metal salt as an electrolytic solution to an anode of the electrolysis reactor;

(2) supplying a carbon dioxide-containing gas to a cathode of the electrolysis reactor;

(3) applying a voltage between the anode and the cathode to generate hydrogen ions, oxygen, and electrons via electrolysis of water in the anode and substituting the metal cations in the Group I metal salt with the hydrogen ions;

(4) transporting the metal cations generated in the anode to the cathode through an ion-exchange membrane and transporting the electrons to the cathode through an external electric line; and (5) reacting carbon dioxide, water, metal cations, and electrons in the cathode to produce carbonate and/or formate; and (6) for the purpose of maintaining the concentration of the Group I metal salt in the electrolytic solution to be supplied to the anode, measuring the pH of the electrolytic solution recovered from the products formed in the anode and replenishing the recovered the electrolytic solution with the aqueous solution of the Group I metal salt according to the pH of the electrolytic solution.

The method according to the present invention may further include recovering the electrolytic solution from the products produced in the anode by gas-liquid separation; and recovering the carbonate and/or formate from the products produced in the cathode by gas-liquid separation.

In the present invention, the water which moved from the anode to the cathode through an ion-exchange membrane and/or water vapor in the carbon dioxide-containing gas may form a water film on the surface of the cathode catalyst layer (FIG. 2). In particular, since the $CO_2$ supplied to the cathode is dissolved in the water film and used as a reactant, the reaction can proceed under thermodynamically favorable conditions such as a liquid-phase reaction, and a separate cathode electrolytic solution is not required.

Additionally, the water which moved from the anode to the cathode through an ion-exchange membrane and/or water vapor in the carbon dioxide-containing gas may promote a spontaneous reduction reaction. As such, the carbon dioxide supplied in a gas state is reduced in a small amount of liquid-phase water film, resulting in a higher concentration of carbonate and/or formate than the conventional liquid-phase reaction.

Furthermore, the reactant, $CO_2$, is transferred to the cathode surface in the gas phase, and the $CO_2$ consumed by the reaction in the water film is continuously replenished by the $CO_2$ gas being supplied, and thus the mass transfer resistance can be minimized without being limited by the solubility.

Additionally, since the activation energy of the reaction is lowered using a minimum amount of water, it is possible to recover the produced carbonate and/or formate at a high concentration. Accordingly, the cost required for separation, purification, and concentration can be reduced.

Meanwhile, the present invention can prepare carbonate and/or formate containing a Group I metal as a cathode product with a high Faradaic efficiency by measuring the pH of the electrolytic solution recovered from the products formed in the anode and replenishing the recovered electrolytic solution with the aqueous solution of the Group I metal salt according to the pH of the electrolytic solution for the purpose of maintaining the concentration of the Group I metal salt in the electrolytic solution to be supplied to the anode. Accordingly, carbonate and/or formate can be produced with a Faradaic efficiency of 80% or higher.

The present invention can perform the reduction reaction of carbon dioxide with a Faradaic efficiency of 80% or higher because the present invention can further promote the spontaneous reduction reaction of carbon dioxide in a liquid-like environment by providing a minimal amount of water due to the formation of a water film on the surface of the cathode.

As used herein, the term "Faradaic efficiency" may refer to the efficiency with which charge (electrons) transfers in a system that performs electrochemical reactions and is also referred to as "Faradaic yield", "coulombic efficiency", or "current efficiency". The Faradaic efficiency can be obtained by comparing a stoichiometric amount of the starting material converted to the product by the applied current with the amount of the product actually measured. That is, in the present invention, the Faradaic efficiency can refer to the conversion efficiency of carbon dioxide to carbonate and/or formate due to the applied current.

Since the pH of the electrolytic solution decreases as the metal cations contained in the electrolytic solution are consumed by the reaction, it is preferable to supply the metal cations to the anode by replenishing the electrolytic solution with the aqueous solution of the Group I metal salt after measuring the pH of the electrolytic solution recovered from the first gas-liquid separator, so as to maintain the concentration of the Group I metal salt in the electrolytic solution in the anode. In particular, it is preferred that the electrolytic solution to be supplied to the anode is an aqueous solution of a Group I metal salt at a concentration of 0.1 M to 2 M.

In the aqueous solution of the Group I metal salt, non-limiting examples of the Group I metal may include Li, Na, K, Rb, Cs, or a mixed metal thereof, and non-limiting examples of the metal salt may include hydrogen carbonate, carbonate, hydrogen carbonate, carbonate, hydroxide salt, chloride salt, sulfate, nitrate, fluoride salt, chlorate, hypochlorite, chlorite, etc.

The electrolysis reactor that performs the electrochemical conversion reaction of carbon dioxide may be an application of an electrochemical battery.

Accordingly, the electrolysis reactor according to a specific embodiment of the present invention may include:

an ion-exchange membrane;
an anode, which comprises an anode catalyst layer applied to a first surface of the ion-exchange membrane; an electrically conductive structure of providing a space for the flow of the electrolytic solution; and a current collector in which a flow path for supplying reactants and a flow path for releasing products are formed; and
a cathode, which comprises a cathode catalyst layer applied to a second surface of the ion-exchange membrane; a gas diffusion layer; and a current collector in which a flow path for supplying reactants and a flow path for releasing products are formed.

For the ion-exchange membrane, a cation-exchange membrane (CEM) may be used, e.g., Nafion® N115, etc.

For the formation of a water film on the surface of the cathode catalyst, the ion-exchange membrane may be prepared using a material which can transport the water contained in the electrolytic solution together with metal cations derived from a Group metal salt, when metal cations are transported from the anode to the cathode.

In the anode, a catalyst having an activity in the electrolysis of water may be used. Accordingly, non-limiting examples of the anode catalyst may include Pt, Pd, Ru, dimensionally stable anode (DSA), Au, Ir, Ag, Rh, Ni, Al, Mo, Cr, Cu, Ti, W, an alloy thereof, or a mixed metal oxide ($Ta_2O_5$, $IrO_2$, etc.).

In the cathode, a catalyst having an activity in the reduction reaction of carbon dioxide may be used. Non-limiting examples of the cathode catalyst for the preparation of carbonate and/or formate may include Sn, Pb, In, Cu, Pt, Pd, Ni Hg, Tl, Cd, Bi, Au, Ag, an oxide thereof, an alloy thereof, an organometallic compound containing the same, etc.

Since the reduction reaction of carbon dioxide competes with the hydrogen generation reaction, it is preferable to use a catalyst having an activity in the reduction reaction of carbon dioxide as a cathode material while having a large overvoltage for the hydrogen generation reaction.

As illustrated in FIG. 2, the cathode may include a cathode catalyst layer applied to a second surface of an ion-exchange membrane; a gas diffusion layer to which the carbon dioxide-containing gas can be evenly supplied (e.g., carbon paper); and a current collector in which a flow path for supplying reactants and releasing products is formed, and the cathode catalyst layer may have various structures (e.g., particles, a porous structure) and surface characteristics so that a water film can be well formed on its surface.

In the present invention, when a carbon dioxide-containing gas is supplied to the cathode through a gas diffusion layer, a gas diffusion layer may be a water-repellent carbon paper.

The carbonate and/or formate produced in the cathode can be prepared in the form of an aqueous solution, and their concentration in the aqueous solution is preferably 0.1 wt % to 50 wt %.

The concentration of the product may be controlled by supplying additional water vapor to the cathode as required by real-time measurement of the concentration of the produced carbonate and/or formate through an ion electrode.

Accordingly, an apparatus according to an embodiment of the present invention can measure the concentration of carbonate and/or formate recovered in the second gas-liquid separator using an ion electrode.

Depending on the concentration of carbonate and/or formate recovered in the second gas-liquid separator, additional water vapor can be supplied to the cathode so that the concentration of the carbonate and/or formate recovered in the second gas-liquid separator can be controlled, preferably to be in the range of 0.1 wt % to 50 wt %.

For example, the concentration of the produced carbonate and/or formate can be measured by ion-selective electrodes, and it is possible to measure the concentration of a specific ion through a potential difference generated when the corresponding ion is selectively bonded to the membrane, using a membrane selectively responsive to the specific ion as an indicator electrode. For example, with regard to the $K^+$ ion-selective electrode, a liquid ion-exchange membrane containing valinomycin that selectively accepts $K^+$ ion may be used as the indicator electrode.

In the present invention, a voltage may be applied so as to generate a potential at which a reduction reaction of carbon dioxide can occur. The voltage applied across the anode and cathode is preferably between 2 volts and 6 volts.

Considering the standard potential of each electrode reaction, a battery voltage of 1.42 V or higher is theoretically required from the standard potential of 1.23 V of the water decomposition reaction occurring in the anode and the standard potential of −0.19 V of the formate generation reaction through the reduction of the carbon dioxide generated in the cathode, and actually, a voltage of 2 V or higher is required due to overvoltage such as electric resistance, activation energy, ion exchange resistance, etc. Additionally, the energy efficiency may be lowered because the reduction potential is formed to be higher than −2.2 V under the battery voltage condition of 6 V or higher, and thus the hydrogen generation reaction is more selective than the carbon dioxide reduction reaction.

The electrical energy for the electrochemical reduction of carbon dioxide may come from conventional energy sources, including conventional nuclear energy sources and alternative energy sources from solar cells or other non-fossil fuel electricity sources (e.g., hydro power, wind power, solar power generation, geothermal, etc.). Preferably, the electricity source can supply a voltage higher than 2 V across the battery. Different voltage values may be adjusted depending on the internal resistance of the battery used.

Advantageous Effects of the Invention

An apparatus and methodof preparing carbon dioxide and/or formate from carbon dioxide according to the present invention can prepare carbonate and/or formate at a high concentration with high Faradaic efficiency, as in the case of a liquid-phase reduction reaction.

BRIEF DESCRIPTION OF DRAWINGS

FIG. 1A is a schematic diagram that thermodynamically explains the limit of the gas-phase reaction of existing carbon dioxide.

The top two graphs in FIG. 1B show the concentrations and Faradaic efficiencies of products in the liquid-phase reaction, and the two bottom graphs show the concentrations and Faradaic efficiencies of products in the gas-phase reaction.

FIG. 2 is a conceptual diagram schematically illustrating the reaction of carbon dioxide occurring in an apparatus and each part of the apparatus according to an embodiment of the present invention.

FIG. 3 is a schematic diagram of an apparatus of preparing formate and carbonate by electrochemically reducing carbon dioxide ($CO_2$) according to an embodiment of the present invention.

FIG. 4 shows the measurement results of concentrations and Faradaic efficiencies according to the amount of water vapor supplied in preparing formate and carbonate by electrochemical reduction of carbon dioxide ($CO_2$) according to the method of the present invention.

BEST MODE

The following Examples are for illustrative purposes only, and the scope of the present invention is not limited by these Examples.

Example 1: Manufacture of Apparatus of Preparing Carbonate and/or Formate by Electrochemical Reduction of Carbon Dioxide According to the Present Invention As illustrated in FIGS. 2 and 3, an apparatus of preparing carbonate ($M_2CO_3$ or $MHCO_3$) and/or formate (HCOOM) by electrochemical reduction of carbon dioxide was manufactured.

An anode electrode was manufactured by spray coating particles of platinum (Pt) catalyst powder on one side of an ion-exchange membrane (Nafion 115) while particulate tin (Sn) powders were coated on the other side to prepare a cathode electrode. A 0.2 mm-thick titanium gauze was inserted into the prepared anode so that the electrolytic solution can be filled with the electrolytic solution, whereas a 0.2 mm-thick water-repellent carbon paper was inserted into a gas diffusion layer and a current collector was bonded thereto. For the current collector, a graphite or brass plate with good electrical conductivity was used to generate a potential difference between the two electrodes when voltage was applied to an electrolysis reactor and the reactant was supplied to the anode and the cathode, and a flow path was formed to discharge the products.

Experimental Example 1: Examination of Efficiency with Regard to Method of Preparing Carbon Dioxide According to the Present Invention The concentrations of carbonate and formate were measured by changing the rate of water vapor supply from 0 mg/min to 502.3 mg/min by applying a 3.0 V voltage at a reactor temperature of 25° C., while supplying $CO_2$ gas at 300 sccm using a apparatus of preparing carbonate and/or formate by electrochemically reducing the carbon dioxide ($CO_2$) produced in Example 1 above.

Specifically, the experimental conditions were as follows:
Applied voltage: 3.0 V
Reaction temperature: 25° C.
Ion-exchange membrane: Nafion 115
Anode electrode catalyst: Spray-coated Pt powder
Cathode electrode catalyst: Spray-coated Sn powder
Electrolytic solution supplied to anode: 0.5 M $KHCO_3$ (aqueous solution)
Gas supplied to cathode: Mixed gas of $CO_2$ water vapor
Amount of water vapor supply: 0 mg/min to 196 mg/min As a result of the analysis of the products using HPLC, it was confirmed that 1% to 2% of carbonate and 3% to 7% of formate were prepared at a Faradaic efficiency of 80% or higher according to the amount of water vapor introduced (FIG. 4).

The invention claimed is:
1. An apparatus for preparing carbonate and/or formate from carbon dioxide ($CO_2$), comprising:

an electrolysis reactor comprising (i) an anode which contains an aqueous solution of a Group I metal salt as an electrolytic solution, (ii) an ion-exchange membrane through which metal cations derived from the Group I metal salt and water flow from the anode to a cathode, (iii) the cathode, and (iv) a gas diffusion layer which supplies a carbon dioxide-containing gas to the cathode;

a power supply unit for applying a voltage between the anode and the cathode;

a first gas-liquid separator for recovering the electrolytic solution from products formed in the anode;

a second gas-liquid separator for recovering carbonate and/or formate from products formed in the cathode;

an ion electrode for measuring the concentration of the carbonate and/or formate recovered from the second gas-liquid separator;

a pH meter for measuring a pH of the electrolytic solution recovered from the first gas-liquid separator;

a first reactant supply unit for supplying (a) the electrolytic solution recovered from the first gas-liquid separator and (b) the aqueous solution of the Group I metal salt with which the recovered electrolytic solution is replenished according to the pH of the electrolytic solution, to the anode; and a second reactant supply unit for supplying carbon dioxide or a mixture comprising carbon dioxide and water vapor to the cathode;

wherein, when a voltage is applied between the anode and the cathode, in the anode, water undergoes electrolysis to generate hydrogen ions, oxygen, and electrons, and the metal cations in the Group I metal salt are substituted with the hydrogen ions, while the generated metal cations move to the cathode through the ion-exchange membrane and the electrons move to the cathode through an external electric line; and in the cathode, the carbon dioxide, water, metal cations, and electrons are reacted and produce carbonate and/or formate;

wherein the apparatus is configured to supply water to the cathode from the anode through the ion-exchange membrane;

wherein the apparatus does not comprise a unit for supplying a cathode electrolytic solution to the cathode;

wherein the electrolysis reactor comprises:

(ii) the ion-exchange membrane;

(i) the anode, which comprises an anode catalyst layer applied to a first surface of (ii) the ion-exchange membrane; an electrically conductive structure for providing a space for the flow of the electrolytic solution; and a current collector in which a flow path for supplying reactants of the water and metal cations and a flow path for releasing the products are formed; and (iii) the cathode, which comprises a cathode catalyst layer applied to a second surface of (ii) the ion-exchange membrane; (iv) the gas diffusion layer; and a current collector in which a flow path for supplying reactants of the carbon dioxide and a flow path for releasing the products are formed;

wherein the water which moves from the anode to the cathode through the ion-exchange membrane, the water vapor in the carbon dioxide-containing gas, or both forms a water film on the surface of a cathode catalyst layer;

wherein the cathode catalyst layer has a particulate structure or a porous structure, and the cathode catalyst layer is configured to promote formation of the water film on the surface of the cathode catalyst layer;

wherein the electrolytic solution to be supplied to the anode is the aqueous solution of a Group I metal salt at a concentration of 0.1 M to 2 M; and wherein the concentration of the carbonate and/or formate recovered from the second gas-liquid separator is regulated by supplying additional water vapor to the cathode according to the concentration of the carbonate and/or formate recovered from the second gas-liquid separator.

2. The apparatus of claim 1, wherein the pH of the electrolytic solution decreases as the metal cations contained in the electrolytic solution supplied to the anode are consumed by the reaction, and for the purpose of maintaining the concentration of the Group I metal salt in the electrolytic solution in the anode, the recovered electrolytic solution to be supplied to the anode is replenished with the aqueous solution of the Group I metal salt according to the measurement of the pH of the electrolytic solution recovered from the first gas-liquid separator.

3. The apparatus of claim 1, wherein a concentration of the carbonate and/or formate recovered from the second gas-liquid separator is regulated to 0.1 wt % to 50 wt %.

4. The apparatus of claim 1, wherein a catalyst of the cathode catalyst layer is selected from the group consisting of Sn, Pb, In, Cu, Pt, Pd, Ni Hg, Tl, Cd, Bi, Au, Ag, an oxide thereof, an alloy thereof, and an organometallic compound containing the same, and wherein a catalyst of the anode catalyst layer is selected from the group consisting of Pt, Pd, Ru, dimensionally stable anode (DSA), Au, Ir, Ag, Rh, Ni, Al, Mo, Cr, Cu, Ti, W, an oxide thereof, an alloy thereof, and a mixed metal oxide thereof.

5. The apparatus of claim 1, wherein the Group I metal in the Group I metal salt is Li, Na, K, Rb, Cs, or a mixed metal thereof, and the metal salt is hydrogen carbonate, carbonate, hydrochloride, chloride salt, sulfate, nitrate, fluoride salt, chlorate, hypochlorite, or chlorite.

6. A method of preparing carbonate and/or formate from carbon dioxide in in the apparatus of claim 1, comprising:

(1) supplying the aqueous solution of the Group I metal salt as the electrolytic solution to the anode of the electrolysis reactor;

(2) supplying the carbon dioxide-containing gas to the cathode of the electrolysis reactor;

(3) applying the voltage between the anode and the cathode to generate the hydrogen ions, oxygen, and electrons via the electrolysis of water in the anode and substituting the metal cations in the Group I metal salt with the hydrogen ions;

(4) transporting the metal cations generated in the anode to the cathode through the ion-exchange membrane and transporting the electrons to the cathode through the external electric line; and (5) reacting carbon dioxide, water, metal cations, and electrons in the cathode to produce the carbonate and/or formate; and (6) for the purpose of maintaining the concentration of the Group I metal salt in the electrolytic solution to be supplied to the anode, measuring the pH of the electrolytic solution recovered from the products formed in the anode and replenishing the recovered the electrolytic solution with the aqueous solution of the Group I metal salt according to the pH of the electrolytic solution.

7. The method of claim 6, wherein the carbonate and/or formate produced in step (5) is produced in the form of an aqueous solution.

8. The method of claim 7, wherein the concentration of the carbonate and/or formate produced in step (5) in the aqueous solution is 0.1 wt % to 50 wt %.

9. The method of claim 6, further comprising:
recovering the electrolytic solution from the products produced in the anode by gas-liquid separation; and
recovering the carbonate and/or formate from the products produced in the cathode by gas-liquid separation.

10. The method of claim 6, wherein the carbonate and/or formate is produced in a Faradaic efficiency of 80% or higher.

11. The method of claim 6, wherein a voltage of 2 V to 6 V is applied to both ends of the anode and the cathode.

12. The method of claim 6, wherein in Step (2), the carbon dioxide-containing gas is supplied to the cathode through the gas diffusion layer; and
the water which moved from the anode to the cathode through the ion-exchange membrane, the water vapor in the carbon dioxide-containing gas, or both forms a water film on the surface of the cathode catalyst layer.

13. The method of claim 6, wherein the electrolysis reactor comprises:
the ion-exchange membrane;
the anode, which comprises the anode catalyst layer applied to the first surface of the ion-exchange membrane; the electrically conductive structure for providing the space for the flow of the electrolytic solution; and the current collector in which a flow path for supplying reactants and a flow path for releasing products are formed; and
the cathode, which comprises the cathode catalyst layer applied to the second surface of the ion-exchange membrane; the gas diffusion layer; and the current collector in which the flow path for supplying reactants and the flow path for releasing products are formed.

14. The method of claim 6, wherein the electrolytic solution supplied to the anode is an aqueous solution of a Group I metal salt at a concentration of 0.1 M to 2 M.

15. The method of claim 6, wherein the apparatus further comprises the ion electrode for measuring the concentration of the carbonate and/or formate recovered from the second gas-liquid separator,
wherein the concentration of the carbonate and/or formate recovered from the second gas-liquid separator is regulated by supplying additional water vapor to the cathode according to the concentration of the carbonate and/or formate recovered from the second gas-liquid separator.

* * * * *